United States Patent
Vasiev et al.

(10) Patent No.: US 12,370,306 B1
(45) Date of Patent: Jul. 29, 2025

(54) HOLD ASSISTANCE DEVICE FOR USE WITH A MEDICAMENT DELIVERY DEVICE

(71) Applicant: Genzyme Corporation, Cambridge, MA (US)

(72) Inventors: Iskandar Vasiev, Melbourn (GB); Kamaal de Silva, Cambridge (GB); Tom Alan Oakley, Cambourne (GB); Adam Christopher Nightingale, Cambridge (GB); Joel John Williams, Cambridge (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/984,873

(22) Filed: Dec. 17, 2024

(51) Int. Cl.
*A61M 5/158* (2006.01)
*A61M 5/32* (2006.01)

(52) U.S. Cl.
CPC .......... *A61M 5/158* (2013.01); *A61M 5/3204* (2013.01); *A61M 2005/1586* (2013.01)

(58) Field of Classification Search
CPC ........ A61M 2005/1586; A61M 5/3204; A61M 5/3202; A61M 2025/09116; A61M 39/286; A61M 2005/3217; A61M 5/3219; A61M 5/3205; A61M 2005/3265; A61M 2005/3267; A61M 5/3271; A61M 5/158
See application file for complete search history.

(56) References Cited

U.S. PATENT DOCUMENTS 4,405,163 A * 9/1983 Voges ................ F16L 37/138
604/905

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

* cited by examiner

Primary Examiner — Theodore J Stigell
(74) Attorney, Agent, or Firm — Fish & Richardson P.C.

(57) ABSTRACT

A hold assistance device for use with a medicament delivery device is described. The hold assistance device includes: a housing configured to be fixedly coupled to a medicament delivery device, the housing comprising: a proximal end and a distal end defining an axial direction, and an inclined surface angled relative to the axial direction; a blocking element moveable along the inclined surface; and an actuation element moveable relative to the housing and arrangeable in an activated position in which the actuation element applies an activation force to the blocking element in a direction towards the distal end, such that movement of the actuation element into the activated position causes the blocking element to move against the inclined surface towards the distal end and to exert a clamping force generally normal to the axial direction.

19 Claims, 7 Drawing Sheets

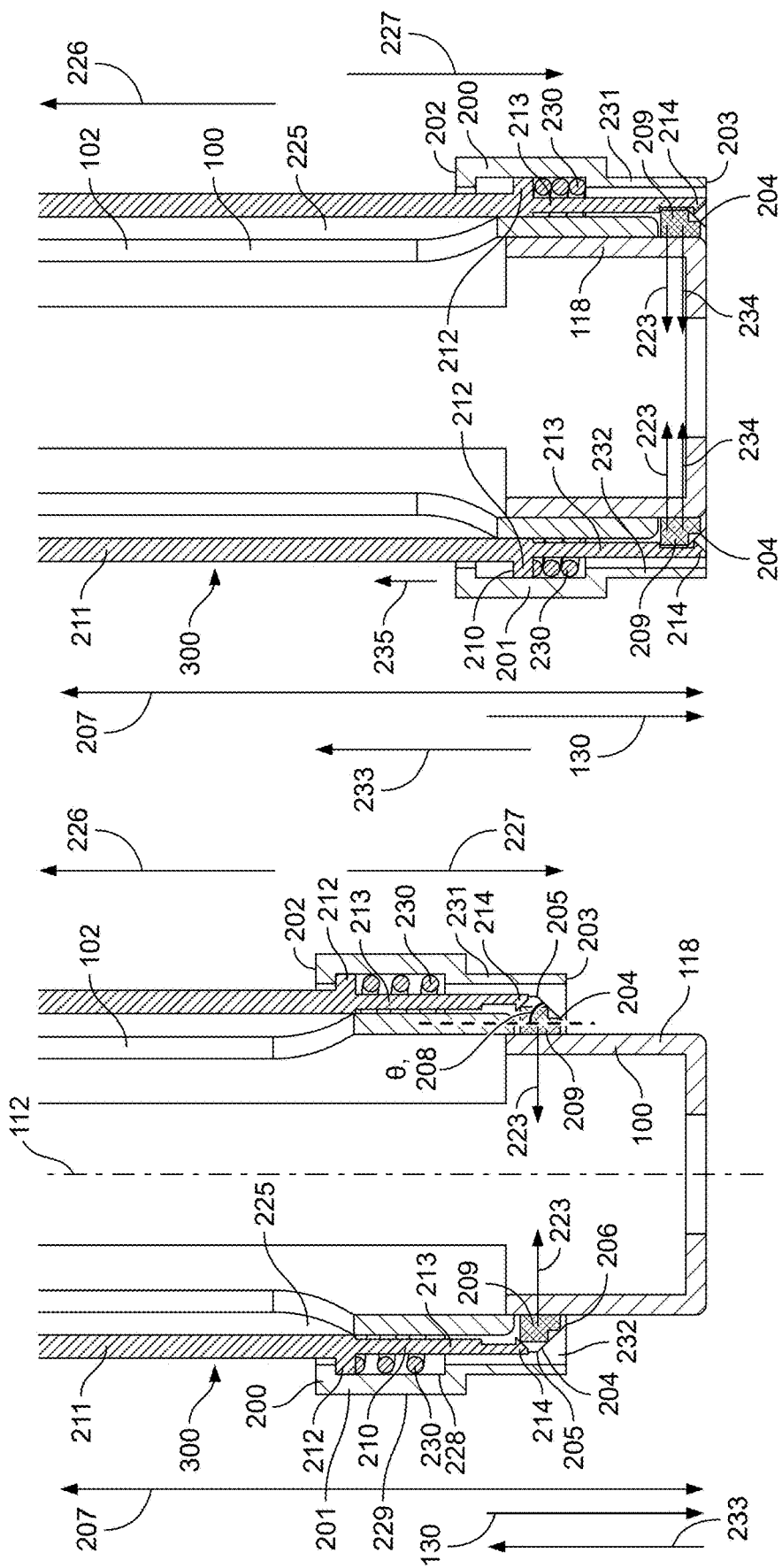

HOLD ASSISTANCE DEVICE FOR USE WITH A MEDICAMENT DELIVERY DEVICE

TECHNICAL FIELD

The present disclosure relates to a hold assistance device for use with a medicament delivery device; to a medicament delivery system comprising a hold assistance device and a medicament delivery device; and to a method of operating a medicament delivery system.

BACKGROUND

Medicament delivery devices can be used to deliver a range of medicaments. In some devices, the device must be held in a holding position at an injection site to ensure that the correct dose of medicament is dispensed from the device, before removing the device from the injection site. It may be difficult to hold the device in the holding position whilst the medicament is dispensed. This may result in pain, discomfort, a wet injection site, early device removal and/or partial delivery of the medicament. Administering an injection involves several risks and challenges, encompassing both mental and physical aspects.

SUMMARY

The present disclosure provides a hold assistance device to assist a user with the holding of a medicament delivery device in the holding position whilst the medicament is dispensed.

A first aspect of this disclosure provides a hold assistance device for use with a medicament delivery device, the hold assistance device comprising: a housing configured to be fixedly coupled to a medicament delivery device, the housing comprising: a proximal end and a distal end defining an axial direction, and an inclined surface angled relative to the axial direction; a blocking element moveable along the inclined surface; and an actuation element moveable relative to the housing and arrangeable in an activated position in which the actuation element applies an activation force to the blocking element in a direction towards the distal end, such that movement of the actuation element into the activated position causes the blocking element to move against the inclined surface towards the distal end and to exert a clamping force generally normal to the axial direction.

Optionally, when the actuation element is in the activated position, movement of the blocking element against the inclined surface towards the proximal end is resisted.

Optionally, when the actuation element is in the activated position, the blocking element is wedged against the inclined surface by the actuation element.

Optionally, when the housing is coupled to a medicament delivery device and the actuation element is in the activated position, the clamping force is configured to act on the medicament delivery device.

Optionally, the hold assistance device comprises a receiving volume for receiving a medicament delivery device, and the clamping force is configured to act towards the receiving volume.

Optionally, the blocking element is configured to be movable relative to the housing in a diagonal direction that is angled relative to the axial direction.

Optionally, the blocking element is configured to be movable relative to the housing along the axial direction, and along a radial direction that is generally normal to the axial direction.

Optionally, the clamping force is a compressive force.

Optionally, the blocking element is configured to provide a frictional force.

Optionally, the frictional force is configured to act along the axial direction, for example away from the distal end and towards the proximal end, in a generally proximal direction.

Optionally, the inclined surface of the housing is arranged to be angled relative to the axial direction by an angle of between approximately 3° and 45°.

Optionally, the coefficient of friction $\mu$ between the inclined surface of the housing and the blocking element is between approximately 0.05 and 1, for example between approximately 0.05 and 0.5.

Optionally, the coefficient of friction $\mu$ between the blocking element and a medicament delivery device coupled to the housing is between approximately 0.05 and 1, for example between approximately 0.05 and 0.5.

Optionally, movement of the blocking element in a radially inwards direction normal to the axial direction causes the clamping force to be increased, and conversely, movement of the blocking element in a radially outwards direction normal to the axial direction causes the clamping force to be decreased.

Optionally, the activation force is configured to act in an axial direction towards the distal end.

Optionally, movement of the actuation element into the activated position causes the blocking element to move in a radially inward direction that is generally normal to the axial direction.

Optionally, the clamping force is configured to act in a radially inward direction that is generally normal to the axial direction.

Optionally, the actuation element is axially movable relative to the housing.

Optionally, the housing comprises an inner surface and an outer surface, the inner surface configured to be fixedly coupled to a medicament delivery device, wherein the inclined surface is arranged to be inclined inwards away from the outer surface and towards the inner surface in a direction away from the proximal end and towards the distal end.

Optionally, the inclined surface is generally straight and linear.

Optionally, at least a portion of the inclined surface is curved.

Optionally, the housing comprises a ramp comprising the inclined surface.

Optionally, the housing comprises a wedge comprising the inclined surface.

Optionally, the inclined surface comprises a proximal end arranged proximate to the proximal end of the housing, and a distal end arranged proximate to the distal end of the housing.

Optionally, the actuation element is configured to cause the blocking element to move along the inclined surface.

Optionally, the actuation element is movable relative to the blocking element.

Optionally, the actuation element comprises a sleeve or push pad.

Optionally, the sleeve or push pad is generally cylindrical.

Optionally, the sleeve or push pad is configured to circumscribe the main body of a medicament delivery device.

Optionally, the sleeve or push pad is configured to be axially movable relative to the main body of a medicament delivery device.

Optionally, the actuation element comprises a flange configured to abut the housing to limit axial movement of the actuation element in the axial direction.

Optionally, the actuation element comprises a flange configured to abut an inner surface of the housing to limit axial movement of the actuation element in a proximal direction away from the distal end and towards the proximal end.

Optionally, the actuation element comprises one or more arms arranged to extend generally parallel to the axial direction, for example two arms, which may be equally spaced apart from one another.

Optionally, the one or more arms are arranged inside the housing.

Optionally, the actuation element comprises one or more heads each integrally formed with or connected to a respective one of the one or more arms.

Optionally, each of the one or more heads is arranged at a distal end of the respective arm, proximate to the distal end of the housing.

Optionally, each of the one or more heads is formed from a flexible or resiliently deformable material.

Optionally, each of the one or more heads is configured to be deflected around the blocking element upon axial movement of the actuation element in the distal direction.

Optionally, each of the one or more heads is configured to be deflected around the blocking element upon axial movement of the actuation element into the activated position.

Optionally, each of the one or more heads comprises an angled edge.

Optionally, each of the one or more heads is configured to be deflected relative to the blocking element upon axial movement of the actuation element in the distal direction, causing the head to hook onto or clip into the blocking element.

Optionally, the blocking element comprises a cut-out, recess, channel, groove or aperture for receiving a respective one of the one or more heads.

Optionally, the hold assistance device further comprises an actuation element biasing member configured to bias the actuation element towards the proximal end of the housing, for example wherein the actuation element biasing member comprises a spring.

Optionally, the actuation element biasing member comprises a compression spring.

Optionally, when the actuation element is in the activated position, the compression spring is arranged to be in a compressed state, and when the actuation element is not in the activated position, the compression spring is arranged to be in an uncompressed state.

Optionally, when the actuation element is arranged in a distal position, the compression spring is arranged to be in a compressed state, and when the actuation element is arranged in a proximal position, the compression spring is arranged to be in an uncompressed state, wherein when the actuation element is arranged in the distal position it is arranged to be closer to the distal end of the housing than when the actuation element is arranged in the proximal position.

Optionally, the actuation element is arrangeable in a release position in which the actuation element applies a release force to the blocking element in a direction towards the proximal end, such that movement of the actuation element from the activated position into the release position permits the blocking element to move along the inclined surface towards the proximal end, wherein when the actuation element is in the release position, movement of the actuation element towards the proximal end causes the blocking element to move relative to the inclined surface towards the proximal end, thus reducing the magnitude of the clamping force.

Optionally, when the actuation element is in the release position, movement of the actuation element along the axial direction away from the distal end and towards the proximal end causes the blocking element to move along the axial direction away from the distal end and towards the proximal end.

Optionally, the actuation element comprises an activation surface for engaging with the blocking element, for example with a proximal end thereof, to apply the activation force to the blocking element.

Optionally, the actuation element comprises a release surface for engaging with the blocking element, for example with a distal end thereof, to apply the release force to the blocking element.

Optionally, the actuation element comprises an activation surface for engaging with a proximal end of the blocking element to apply the activation force to the blocking element, and a release surface for engaging with a distal end of the blocking element to apply the release force to the blocking element.

Optionally, the activation surface and the release surface are arranged to be generally normal to the axial direction and to be generally parallel to one another.

Optionally, each of one or more arms of the actuation element comprises an activation surface and a release surface.

Optionally, the activation force is configured to be a pushing force.

Optionally, the release force is configured to be a pulling force.

Optionally, movement of the actuation element from the activated position to the release position permits the blocking element to move in a radially outward direction that is generally normal to the axial direction.

Optionally, the actuation element comprises a receiving space for receiving the blocking element, wherein the receiving space comprises the activation surface and the release surface.

Optionally, the receiving space comprises a cut-out, recess or groove in the actuation element.

Optionally, each of one or more arms of the actuation element is generally elongate, and each of said one or more arms comprises a respective receiving space.

Optionally, the receiving space is axially longer than the blocking element, such that when the actuation element is in the activated position the activation surface is in contact with the blocking element but the release surface is not in contact with the blocking element, and such that when the actuation element is in the release position the release surface is in contact with the blocking element but the activation surface is not in contact with the blocking element.

Optionally, the actuation element is arrangeable in a pre-activated position in which neither the activation surface nor the release surface is engaged with the blocking element, such that movement of the actuation element from the pre-activated position into the activated position causes the activation surface to engage with the blocking element, and such that movement of the actuation element from the activated position into the release position causes the release surface to engage with the blocking element.

Optionally, when the hold assistance device is coupled to a medicament delivery device, the actuation element is configured to initially be in the pre-activated position when a needle cover of the medicament delivery device is in an extended position, for example before delivery of a medicament from a needle of the medicament delivery device has taken place.

Optionally, when the actuation element is in the pre-activated position, the blocking element is arranged to be closer to the distal end of the housing than the actuation element.

Optionally, when the actuation element is arranged in the activated position, the actuation element is arranged to prevent the blocking element from moving against the inclined surface towards the proximal end.

Optionally, when the actuation element is arranged in the pre-activated position, the actuation element is arranged to permit the blocking element to move against the inclined surface towards the proximal end and towards the distal end.

Optionally, when the actuation element is arranged in the pre-activated position, the actuation element is arranged to permit the blocking element to move in the axial direction.

Optionally, the blocking element is arranged inside the housing.

Optionally, the inclined surface is configured to guide and at least partially restrict movement of the blocking element relative to the housing.

Optionally, the blocking element comprises a generally wedge shaped block.

Optionally, the blocking element comprises an inclined surface arranged to be generally parallel to the inclined surface of the housing.

Optionally, the inclined surface of the blocking element is configured to abut or interface with the inclined surface of the housing.

Optionally, the blocking element comprises a roller, a cylinder, a sphere, a ball, a ball bearing, a split ring, a block, and/or a wedge.

Optionally, the blocking element is generally cylindrical, block shaped, cuboidal, wedge shaped, or annular.

Optionally, the blocking element is generally annular and is configured to circumscribe a medicament delivery device received in the housing.

Optionally, the hold assistance device comprises a plurality of blocking elements spaced apart from one another about a longitudinal axis of the hold assistance device.

Optionally, the hold assistance device comprises two blocking elements which are diametrically opposed to one another about a longitudinal axis of the hold assistance device.

Optionally, the blocking element comprises a clutch.

Optionally, the blocking element comprises a sprag clutch.

Optionally, the hold assistance device comprises a receiving volume for receiving a medicament delivery device.

Optionally, the hold assistance device is configured to circumscribe at least a portion of a medicament delivery device.

Optionally, the housing is configured to be removably coupled to a medicament delivery device.

Optionally, the housing is configured to be coupled to a medicament delivery device by a slidably receivable connection.

Optionally, the housing is configured to remain stationary relative to a main body of a medicament delivery device.

Optionally, the housing comprises a generally cylindrical portion.

Optionally, the housing comprises a side portion arranged to protrude from the generally cylindrical portion.

Optionally, the side portion comprises the inclined surface.

Optionally, the actuation element is configured to be moved into the activated position by pressing the hold assistance device against a surface, for example against the skin of a patient.

A second aspect of this disclosure provides a medicament delivery system comprising the hold assistance device of the first aspect of this disclosure, and a medicament delivery device. The medicament delivery device comprises: a main body configured to receive a medicament cartridge and comprising a proximal end and a distal end; a needle for delivery of medicament from the medicament cartridge; a needle cover axially movable relative to the main body between: an extended position in which the needle cover extends from the distal end of the main body and covers a distal end of the needle which protrudes from the main body; and a retracted position in which the needle cover is arranged in a proximal position relative to the extended position such that the distal end of the needle protrudes from a distal end of the needle cover; and a needle cover biasing member configured to bias the needle cover axially in the distal direction towards the extended position. The housing of the hold assistance device is configured to be coupled to the main body, and when the housing is coupled to the main body, the clamping force is configured to act on the needle cover to resist movement of the needle cover axially in the distal direction towards the extended position.

Optionally, the hold assistance device comprises one or more of the optional features recited above in relation to the first aspect of this disclosure.

Optionally, the needle cover biasing member comprises one or more springs, for example a compression spring.

Optionally, the needle cover biasing member comprises a spring, and when the actuation element is in the activated position, the spring is configured to be compressed.

Optionally, when the actuation element is in a pre-activated position, the spring is configured to be in an uncompressed state.

Optionally, when the actuation element is in a release position, the spring is configured to be in an uncompressed state.

Optionally, the blocking element is configured to exert a frictional force on the needle cover.

Optionally, the frictional force is configured to act generally in an opposite direction to a biasing force of the needle cover biasing member.

Optionally, when the actuation element is in the activated position, the blocking element is configured to exert a frictional force along the axial direction in a first direction and a second direction, wherein the frictional force in the first direction is greater than the frictional force in the second direction.

Optionally, the first direction is away from the distal end and towards the proximal end, and the second direction is away from the proximal end and towards the distal end.

Optionally, the housing is configured to remain stationary relative to the main body, when the hold assistance device is coupled to the medicament delivery device.

Optionally, the hold assistance device is removably couplable to the medicament delivery device.

Optionally, the blocking element is arrangeable relative to the medicament delivery device in a first position in which the blocking element and the needle cover are in a clearance fit, and in a second position in which the blocking element and the needle cover are in an interference fit.

Optionally, when the blocking element and the needle cover are in an interference fit, the blocking element is arranged to exert the clamping force on the needle cover.

Optionally, when the blocking element and the needle cover are in a clearance fit, the clamping force on the needle cover is removed, or is at least reduced in magnitude.

Optionally, when the actuation element is in the activated position, the blocking element and the needle cover are configured to be in an interference fit.

Optionally, the coefficient of friction μ between the blocking element and the needle cover is between approximately 0.05 and 1, for example between approximately 0.05 and 0.5.

Optionally, the needle cover biasing member is configured to exert a biasing force to bias the needle cover axially in the distal direction towards the extended position.

Optionally, the biasing force is between approximately 10 N and 15 N.

Optionally, the hold assistance device is generally cylindrical.

Optionally, the hold assistance device is generally annular.

Optionally, the hold assistance device is configured to be arranged at a distal end of a medicament delivery device.

Optionally, the medicament delivery system further comprises a medicament cartridge containing medicament.

A third aspect of this disclosure provides a method of operating a medicament delivery system as in the second aspect of this disclosure, the method comprising: coupling the housing to the main body; moving the needle cover from the extended position to the retracted position; moving the actuation element into the activated position such that the blocking element exerts the clamping force on the needle cover; and releasing the clamping force acting on the needle cover by moving the actuation element from the activated position into a release position in which the actuation element applies a release force to the blocking element in a direction towards the proximal end, such that movement of the actuation element from the activated position into the release position permits the blocking element to move along the inclined surface towards the proximal end, wherein when the actuation element is in the release position, movement of the actuation element towards the proximal end causes the blocking element to move along the inclined surface towards the proximal end, thus reducing the magnitude of the clamping force.

Optionally, the step of moving the needle cover from the extended position to the retracted position causes the needle cover to retract inside the main body such that the needle is exposed, which may be to place the medicament delivery device in a state ready for medicament to be delivered from the needle to an injection site of a patient.

Optionally, the step of moving the needle cover from the extended position to the retracted position comprises placing the medicament delivery device against a surface, for example against the skin of a patient at an injection site, and applying a force in the distal direction towards the surface, thus pushing the needle cover against the surface and causing it to be pushed inside the main body to retract thereinside.

Optionally, the step of moving the actuation element into the activated position such that the blocking element exerts the clamping force on the needle cover is configured to occur simultaneously with the step of moving the needle cover from the extended position to the retracted position.

Optionally, the step of moving the actuation element into the activated position such that the blocking element exerts the clamping force on the needle cover is configured to be caused by or to happen after the completion of the step of moving the needle cover from the extended position to the retracted position.

Optionally, the method further comprises a step of holding the medicament delivery device for a required duration of time at an injection site of a patient. For example, the method may comprise holding the medicament delivery device at an injection site for the amount of time required for completion of delivery of a medicament from the needle to be complete.

Optionally, the step of holding the medicament delivery device for a required duration of time at an injection site of a patient occurs after the step of moving the actuation element into the activated position and before the step of releasing the clamping force on the needle cover by moving the actuation element from the activated position into the release position.

Optionally, the step of releasing the clamping force acting on the needle cover by moving the actuation element from the activated position into the release position comprises removing a user hold force acting on the medicament delivery device.

Optionally, the step of releasing the clamping force acting on the needle cover by moving the actuation element from the activated position into the release position comprises moving the medicament delivery device away from a surface, for example away from the skin of a patient at an injection site.

BRIEF DESCRIPTION OF THE DRAWINGS

Embodiments will now be described, by way of example only, with reference to the accompanying drawings, in which:

FIG. 4A shows a cross-sectional schematic view of a medicament delivery system;

FIG. 4B shows a cross-sectional schematic view of a medicament delivery system;

DETAILED DESCRIPTION

Figure 1:
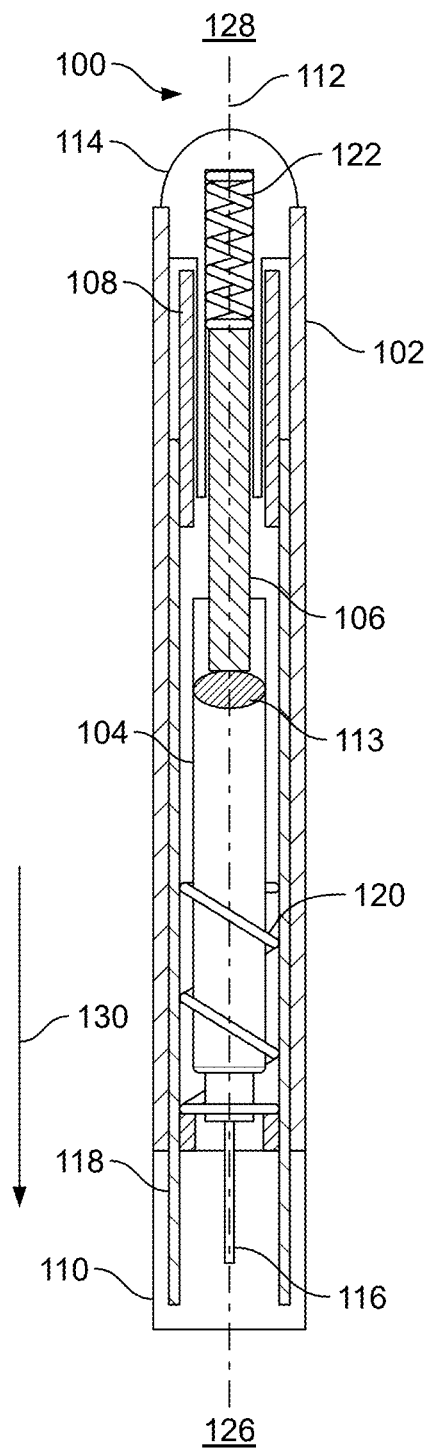
FIG. 1 shows a cross-sectional schematic view of a medicament delivery device.

A drug delivery device (also referred to as an injection device), as described herein, may be configured to inject a medicament into a subject such as a human or animal. For example, delivery could be sub-cutaneous, intra-muscular, or intravenous. Such a device could be operated by a user, who may or may not be the subject. In examples where the user is not the subject, the user may be a care-giver such as a nurse or physician. The device can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Auto-injectors require user actions to commence medicament delivery. One of these actions may involve a user placing a needle cover (also referred to as a needle shroud or needle sleeve) against an injection site of a subject and applying an axial force to the device to cause the needle cover to retract into the housing of the device. As the needle cover retracts into the housing, the needle of the device extends beyond the needle cover and penetrates the injection site of the subject (e.g. the subject's skin). Medicament delivery may be automatically initiated in response to the retraction of the needle cover or in response to some other action by the user, for example the user pressing a button on the device. Once medicament delivery has been initiated, a medicament delivery mechanism will cause medicament contained within the device to be injected into the subject via the needle. The user should hold the device steady with respect to the injection site during the course of medicament delivery to ensure the needle remains steady within the subject. This is to minimise pain and/or discomfort for the subject, and to prevent a wet injection site, early device removal and/or partial medicament delivery.

After the device is removed from injection site, many autoinjectors cover the needle with the needle cover/needle shroud, which is extended out of the device by a control spring. During activation of the device and while holding the device steady during medicament delivery, the user must counteract the biasing force applied by the control spring to the needle cover. However, some users such as those with impaired dexterity may find it difficult to hold the device steady for a relatively long period of time during medicament delivery. It may be beneficial to provide a device which is easier to handle during medicament delivery. However, simply reducing the biasing force produced by the control spring to the needle cover risks accidental actuation and needle safety issues. Therefore, it is desirable to provide a means to help a user of the device hold the device steady, by reducing the force needed to be applied by the user to overcome the biasing force. It is also desirable to reduce the user hold force, whilst minimising or removing any effect on the inserted needle depth, which can impact on the pharmacokinetic profile of the injected medicament and which does not require, or requires very minimal, casework modifications to the injection device.

FIG. 1 shows a schematic example of a cross section of a medicament delivery device 100 (hereinafter referred to as an injection device) according to one or more aspects of the present disclosure. The injection device 100 is configured to inject a medicament into a subject. The injection device 100 comprises an outer casing 102 (also referred to as a housing or injection device body) that encloses a reservoir 104, a plunger 106 and a rotatable collar 108. The reservoir 104 typically contains the medicament to be injected, and may, for example, be in the form of a syringe. The injection device 100 can also include a cap assembly 110 that can be detachably mounted to the outer casing 102. A user typically removes cap 110 from the outer casing 102 before device 100 is operated.

As shown, the outer casing 102 is substantially cylindrical and has a substantially constant diameter along the longitudinal axis of the device 100. The injection device 100 has a distal region 126 and a proximal region 128. The term "distal" refers to a location that is relatively closer to a site of injection, and the term "proximal" refers to a location that is relatively further away from the injection site.

The outer casing 102 is closed at a proximal end by a rear casing 114. A needle 116 and a retractable needle cover 118 (also referred to as a "needle sleeve" or "needle cover") extend from a distal end of the outer casing 102. The retractable needle cover 118 is biased axially in the distal direction of the injection device 100, for example using a control spring 120, which may also be referred to as a needle cover biasing member 120. The needle cover 118 is coupled to the outer casing 102 to permit axial movement of needle cover 118 relative to the outer casing 102. For example, the cover 118 can move in a longitudinal direction parallel to longitudinal axis 112. Specifically, movement of cover 118 in a proximal direction relative to the outer casing 102 can cause a needle 116 to extend from distal region of the outer casing 102, and outside a distal end of the cover 118.

The plunger 106 is biased towards the distal end of the injection device 100 by a biasing means, for example comprising a drive spring 122. The plunger 106 is retained in an initial position by a combination of the rear casing 114 and the collar 108, preventing the biasing means from displacing the plunger 106 in the distal direction. Activation of the injection device 100 causes the collar 108 to rotate, which releases the plunger 106. Once released, the biasing means causes the plunger 106 to move in the distal direction (i.e., towards the needle 116 end of the injection device 100). The plunger 106 contacts a stopper 113 in the reservoir 104, displacing the stopper 113 in the distal direction and causing medicament stored in the reservoir 104 to be expelled from the injection device 100 via the needle 116.

Activation of the injection device 100 can occur via several mechanisms. For example, the needle 116 may be fixedly located relative to the outer casing 102 and initially be located within an extended needle cover 118. Proximal movement of the needle cover 118 by placing a distal end of the cover 118 against an injection site of the subject and moving the outer casing 102 in a distal direction will uncover the distal end of the needle 116. Such relative movement allows the distal end of the needle 116 to extend into the injection site. Such insertion is termed "manual" insertion as the needle 116 is manually inserted via the user's manual movement of the outer casing 102 relative to cover 118. Retraction of the cover 118 into the outer casing 102 causes the collar 108 to rotate, releasing the plunger 106.

Another form of activation is "automated", whereby the needle 116 moves relative to outer casing 102. Such insertion can be triggered by movement of the cover 118 and/or by another form of activation, for example, user actuation of a button (not shown) of the injection device 100.

Typically, the user presses the needle cover 118 against an injection site to push the needle cover 118 at least partially into the outer casing 102. The exposed needle 116 is pushed into the injection site of the subject. In a holding position, medicament is automatically dispensed from the needle 116 via an automated mechanism. A user typically holds the needle cover 118 in the holding position for a predetermined period of time, to ensure that the correct dose of medicament is dispensed from the device 100, before removing the device 100 from the injection site.

The spring biasing force 130 from the control spring 120 against which the user applies a force to move the needle cover 118 is one component of an "activation force" of the device 100. The activation force refers to the force or force profile that the user exerts on the device 100 to move the needle cover 118 from the extended position shown in FIG. 1 to a retracted position within the outer casing 102 for medicament delivery (see for example FIG. 4B). If this force or force profile is not well balanced, it can lead to difficulty in activating the device 100 for some users, or increase the pain or anxiety associated with using the device 100.

Figure 2:
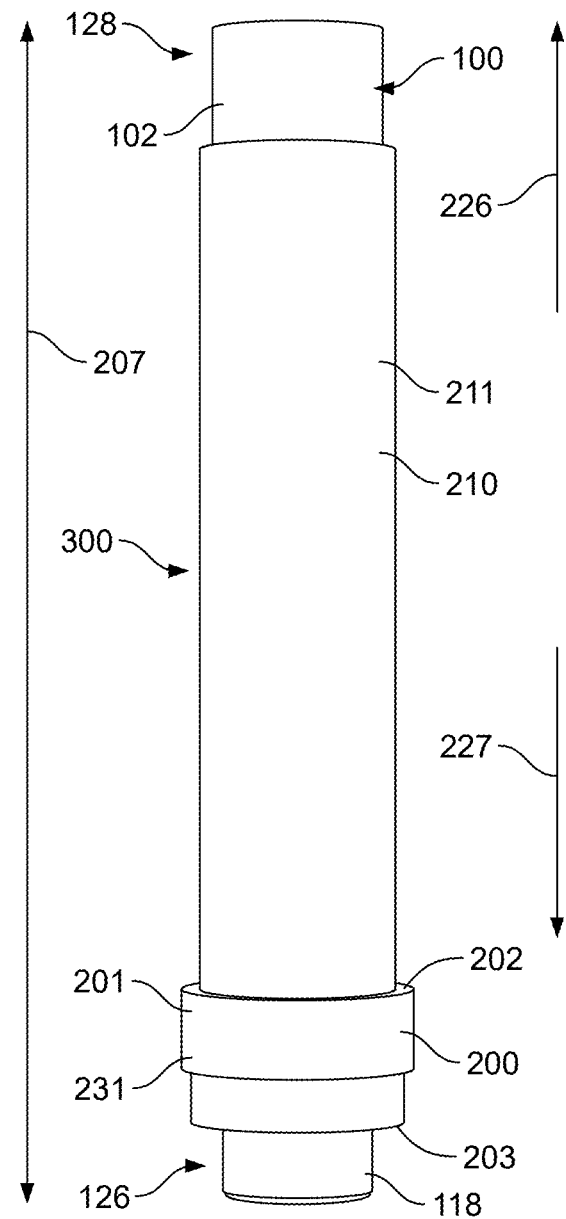
FIG. 2 shows a medicament delivery system.
Figure 3:
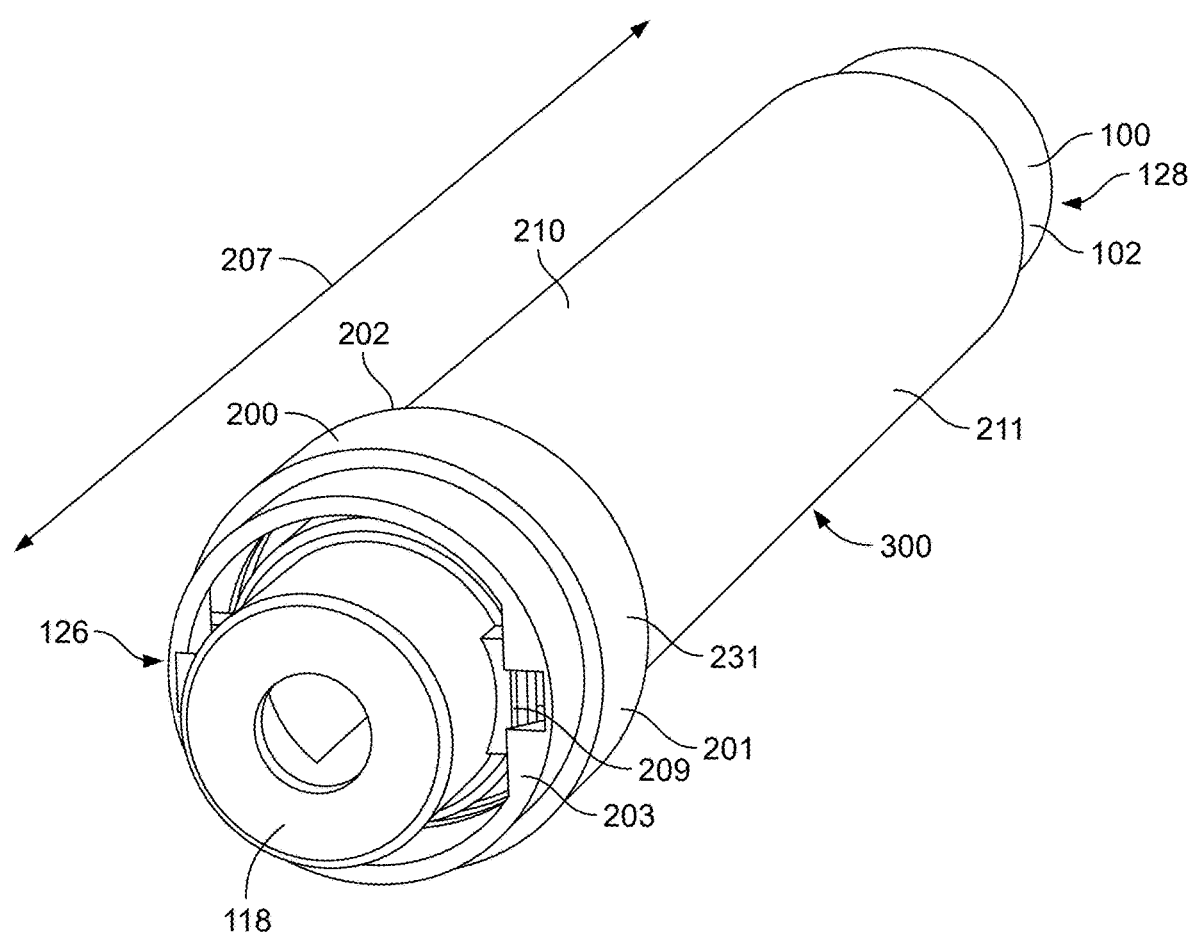
FIG. 3 shows a medicament delivery system.

Following injection, the needle 116 can be retracted within the cover 118. Retraction can occur when the cover 118 moves distally under the biasing of the control spring 120, i.e. under the action of the biasing force 130, as a user removes the device 100 from the injection site of the subject. Once a distal end of the cover 118 has moved past a distal end of the needle 116 such that the needle 116 is covered, the cover 118 may be locked in its extended position to prevent any (substantial) proximal movement of the cover 118 relative to the outer casing 102 (i.e., preventing any movement of the cover 118 that would uncover the needle 116). The cover 118 may be locked by a needle cover non-return element (not shown), such as a catch. FIGS. 2 and 3 show a medicament delivery system 300 comprising a medicament delivery device 100 and a hold assistance device 200. The hold assistance device 200 has a receiving volume 225 (see FIG. 4A) for receiving the medicament delivery device 100. The medicament delivery device 100 may be substantially similar or identical to the injection device 100 shown in FIG. 1 and described above, in which like reference numerals denote alike elements. In the example shown, the medicament delivery device 100 and the hold assistance device 200 are configured to fit together to form the medicament delivery system 300, such that the hold assistance device 200 is arranged to circumscribe at least a portion of the medicament delivery device 100. The hold assistance device 200 may be configured to be assembled together with the medicament delivery device 100 to be supplied to a user as the medicament delivery system 300, or the hold assistance device 200 and the medicament delivery device 100 may be supplied separately to a user and the user may then assemble the hold assistance device 200 and the medicament delivery device 100 together to form the medicament delivery system 300. It is also envisaged that the hold assistance device 200 may be retrofitted to a medicament delivery device 100, and that the hold assistance device 200 may be used with medicament delivery devices other than that in the example shown in FIG. 1 and described above. In any case, it is envisaged that the hold assistance device 200 may be removable from the medicament delivery device 100, such that the hold assistance device 200 may be reusable. The hold assistance device 200 may also be disposable. The function of the hold assistance device 200 is that it serves to assist the user in the use of the medicament delivery device 100, as outlined below.

FIG. 4A shows a cross-sectional schematic view of an exemplary hold assistance device 200 as attached to a medicament delivery device 100. For the sake of clarity and conciseness, only the main body 102 and the needle cover 118 of the medicament delivery device 100 are shown. The needle cover biasing member 120, for example a spring, is arranged to bias the needle cover 118 towards an extended position (see FIGS. 1 and 4A for example) in which the needle cover 118 protrudes from the main body 102 at a distal end 126 of the medicament delivery device 100 such that the needle 116 is covered by the needle cover 118. For example, when the needle cover 118 is in the extended position the needle cover biasing member 120, may for example be a compression spring in its natural extended, uncompressed state. Thus, when the needle cover 118 is in a retracted position (see FIG. 4B for example) in which the needle cover 118 is retracted in a proximal position relative to the extended position such that the needle cover 118 is retracted inside the main body 102 and the needle 116 is not covered by the needle cover 118, this goes against the biasing action of the needle cover biasing member 120. For example, where the needle cover biasing member 120 is a compression spring, this causes the needle cover biasing member 120 to be compressed.

Figure 4C:
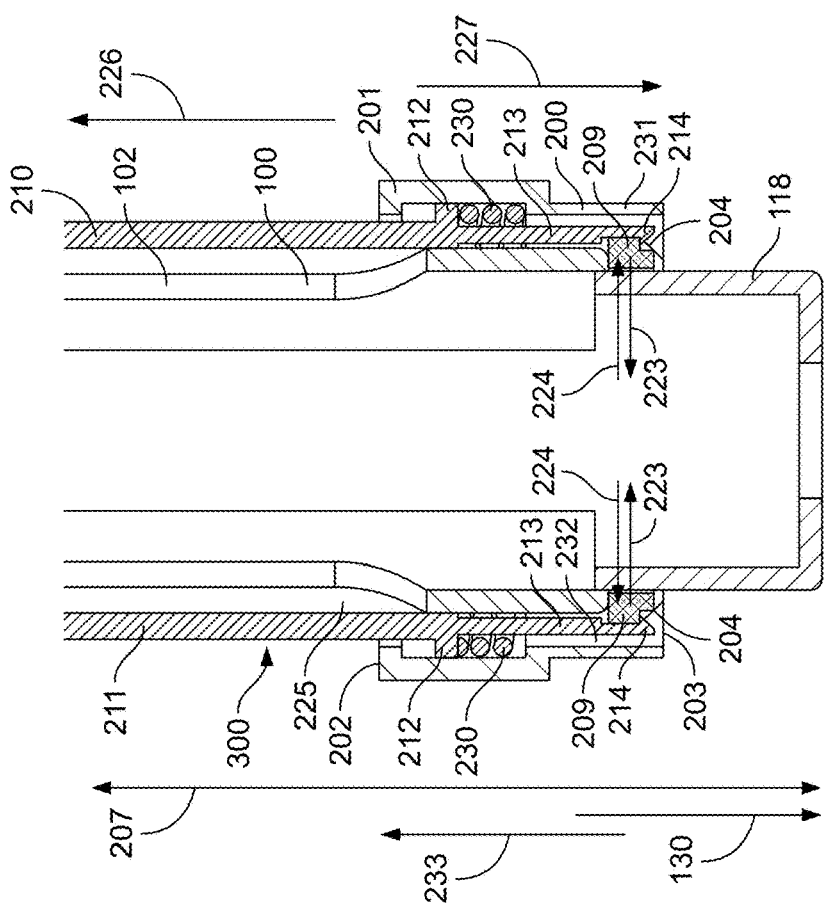
FIG. 4C shows a cross-sectional schematic view of a medicament delivery system

Thus, a biasing force 130, for example a spring force 130, which acts in the direction shown in FIGS. 1 and 4A to 4C for example by the arrow 130, will inherently bias the needle cover 118 back towards the extended position shown in FIGS. 1 and 4A. That is, because moving the needle cover 118 from the extended position to the retracted position goes against the action of the needle cover biasing member 120, for example by compressing a spring, the needle cover biasing member 120 hence biases the needle cover 118 axially in the distal direction 227 towards the extended position. Thus, once the needle cover 118 has been placed into the retracted position, in order to maintain the needle cover 118 in the retracted position so that the needle 116 remains uncovered and can be used for the required duration of time to deliver medicament to a patient, force is required by the user in order to counteract the biasing force 130, to prevent the needle cover 118 from extending outwards again.

Figure 5A:
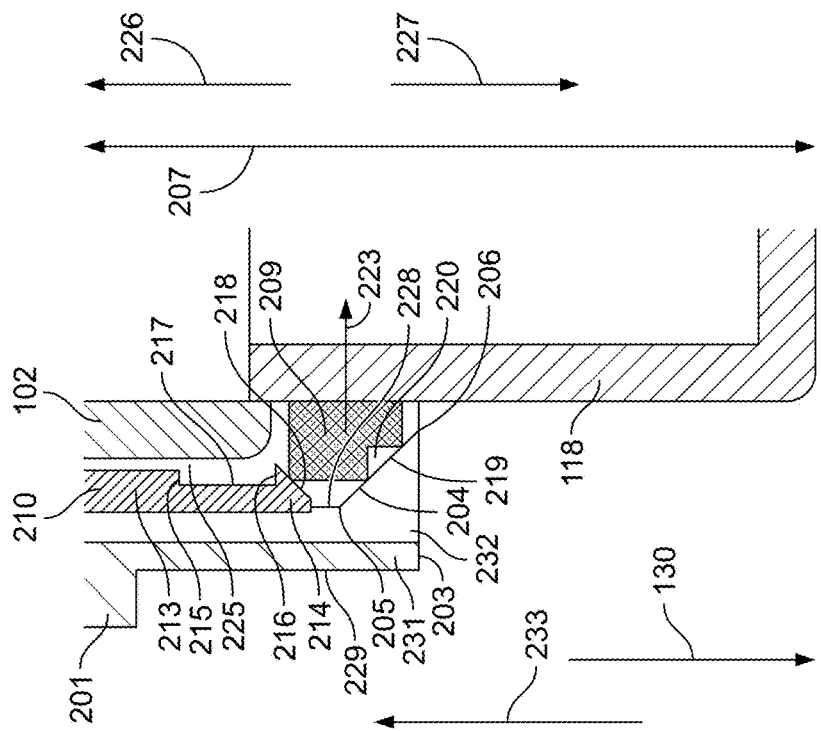
FIG. 5A shows a cross-sectional schematic view of a medicament delivery system.
Figure 5C:
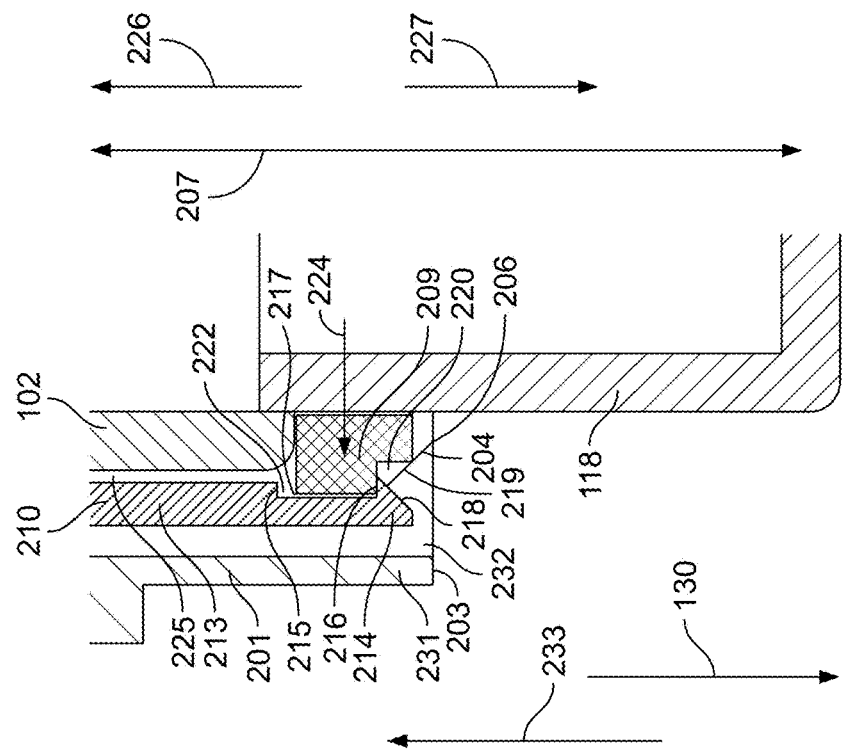
FIG. 5C shows a cross-sectional schematic view of a medicament delivery system.
Figure 5B:
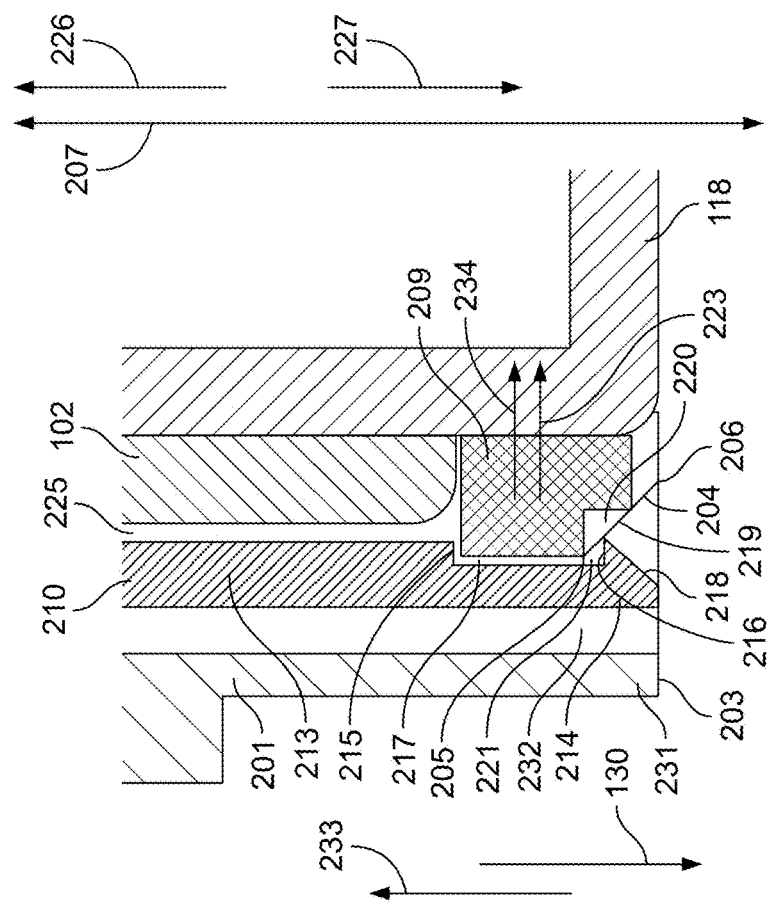
FIG. 5B shows a cross-sectional schematic view of a medicament delivery system.

The hold assistance device 200 acts to counteract the biasing force 130, by providing a resistive force thereagainst, in the form of a radially inward clamping force 234 acting in the direction shown by the arrows 234 in FIGS. 4B and 5B for example. The clamping force 234 acts on the needle cover 118, and thus provides a frictional force 233 acting in the direction shown by the arrow 233, which acts generally in the opposite direction to the biasing force 130 and hence resists movement of the needle cover 118 in the proximal direction 226 from the extended position towards the retracted position.

In this manner, the hold assistance device 200 reduces the amount of force required from a user to hold the medicament delivery device 100 in a medicament delivery state in which the needle cover 118 is retracted, i.e. reduces the amount of force which needs to be applied by the user to resist the biasing force 130. The hold assistance device 200 does this by clamping the needle cover 118 in place by a clamping force 234, thus providing a frictional force 233 which acts generally in an opposite direction to the biasing force 130 in order to hold the needle cover 118 in the retracted position, to prevent it from inadvertently moving towards the distal end 126 of the medicament delivery device 100, until medicament delivery is complete, at which point the needle cover 118 may be allowed to retract again under the action of the needle cover biasing member 120. In other words, the hold assistance device 200 provides a force 233 which can offset the user holding force of a standard two-step autoinjector. The force 233 is configured to act generally in a direction away from the distal end 126 and towards the proximal end 128, i.e. in a generally proximal direction 226.

Exemplary structures of the hold assistance device 200 which can provide for the resistance against the biasing force 130 shall now be described. FIGS. 4A to 4C show cross-sectional schematic views of an example of a hold assistance device 200 which provides such a resistive counterforce against the biasing force 130 of the needle cover biasing member 120, in the form of a clamping force 234, to cause a frictional force 233 to act against distal movement of the needle cover 118 from the retracted position towards the extended position. In the example shown, the hold assistance device 200 comprises a housing 201 which is configured to be coupled to the main body 102 of the medicament delivery device 100, for example by a slidably receivable connection. The housing 201 is configured to remain fixed, i.e. stationary, relative to the main body 102—i.e. the housing 201 is not movable relative to the main body 102 when the hold assistance device 200 is coupled to the medicament delivery device 100. The connection between the housing 201 and the main body 102 may though be configured to be removable, such that the hold assistance device 200 may be removed from the medicament delivery device 100.

The housing 201 comprises a proximal end 202 and a distal end 203, which define an axial direction 207. That is, the axial direction 207 is oriented to extend linearly between the proximal end 202 and the distal end 203. Hereinafter, movement in the axial direction 207 away from the distal end 203 and towards the proximal end 202 may be referred to as movement in a proximal direction 226, and movement in the axial direction 207 away from the proximal end 202 and towards the distal end 203 may be referred to as movement in a distal direction 227. The housing 201 may comprise a generally cylindrical portion 231 arranged to circumscribe the main body 102 of the medicament delivery device 100, and a side portion 232 arranged to protrude from the cylindrical portion 231 (see FIG. 7 for example). Referring back to FIG. 4A, in the example described herein, the side portion 232 is generally circumferentially continuous and extends around the entire circumference of the cylindrical portion 231. Though, it is also envisaged that the side portion 232 may extend around a smaller segment of the circumference of the cylindrical portion 231, for example as in FIG. 7. The side portion 232 may also comprise two or more discrete portions spaced apart from one another about the circumference of the cylindrical portion 231—for example, two discrete portions arranged on opposite sides thereof.

Turning back to FIG. 4A, the housing 201 comprises an inner surface 228 and an outer surface 229. The inner surface 228 is configured to be fixedly coupled to the medicament delivery device 100 and to interface therewith. That is, the inner surface 228 is arranged to be closer to the main body 102 than the outer surface 229. The housing 201 further comprises an inclined surface 204, which may for example be formed in the side portion 232, although it may be formed in any other portion of the housing 201. The inclined surface 204 is angled relative to the axial direction 207 by an angle θ 208. The inclined surface 204 is oriented to be inclined inwards away from the outer surface 229 and towards the inner surface 228 in a direction away from the proximal end 202 of the housing 201 and towards the distal end 203 of the housing. In other words, relative to the central longitudinal axis 112 of the medicament delivery device 100, the inclined surface 204 has a relatively larger radius closer to the proximal end 202 compared with a relatively smaller radius closer to the distal end 203 of the housing 201. That is, along the distal direction 227, the inclined surface 204 is arranged to extend radially inwards towards the longitudinal axis 112. In the example shown, the inclined surface 204 is configured to be generally straight and linear. However, it is also envisaged that the inclined surface may be curved. The inclined surface 204 has a proximal end 205 arranged proximate to the proximal end 202 of the housing 201, and a distal end 206 arranged proximate to the distal end 203 of the housing 201.

The hold assistance device 200 further comprises a blocking element 209 which is arranged inside the housing 201, such that when the hold assistance device 200 is coupled to a medicament delivery device 100, the blocking element 209 is arranged between the housing 201 and the needle cover 118. The blocking element 209 is configured to be movable along the inclined surface 204, such that the blocking element 209 is movable relative to the housing 201, proximate to and generally against the inclined surface 204. That is, the movement of the blocking element 209 is at least partially restricted and guided by the inclined surface 204. In the example shown, the blocking element 209 comprises a generally wedge shaped block comprising an inclined surface 219 (see FIG. 5A). The inclined surface 219 is arranged to be generally parallel to the inclined surface 204, such that the inclined surfaces 204 and 219 are both angled relative to the axial direction 207 by approximately the same angle θ 208. In this manner, the blocking element 209 is configured to be slidable along the inclined surface 204 between the proximal and distal ends 205, 206 thereof, for example by the inclined surface 219 interfacing with the inclined surface 204. However, it is also envisaged that the inclined surface 219 need not necessarily be present, and that the blocking element 209 may have any other suitable shape and may be configured to move relative to the inclined surface 204 to abut the inclined surface 204 or to be at least partially spaced apart therefrom.

Furthermore, whilst the example shown in FIGS. 4A to 4C comprises two blocking elements 209, it is also envisaged that the hold assistance device 200 may comprise any number of one or more blocking elements 209. For example, the hold assistance device 200 may comprise a single blocking element 209, which may for example be generally annular and arranged to circumscribe the needle cover 118, or which may comprise a wedge shaped block. As another example, the hold assistance device 200 may comprise any suitable number of a plurality of blocking elements 209, for example two, three, four, five, six or more blocking elements 209. The plurality of blocking elements 209 may be arranged in any suitable spatial arrangement, for example they may be arranged to be equally or irregularly spaced apart from one another. It is also envisaged that each of the one or more blocking elements 209 need not necessarily be a generally wedge shaped block, and that as aforementioned, an inclined surface 219 need not necessarily be present. That is, each of the one or more blocking elements 209 may have any other suitable shape. Other examples of shapes of blocking elements 209 are described below in relation to FIGS. 7 to 10B.

In the example shown, the hold assistance device 200 comprises two blocking elements 209 arranged on opposite sides of the hold assistance device 200 about the longitudinal axis 112, i.e. they are diametrically opposed. The subsequent description thereof shall refer to just one of the blocking elements 209, although it is to be understood that this description also applies to the other blocking element 209 too and to any other blocking elements 209 which may also be present.

Turning back to the example illustrated in FIG. 4A, the blocking element 209 is configured to move in an angled or diagonal direction relative to the axial direction 207, the angled or diagonal direction having both an axial component and a radial component. That is, the blocking element 209 is configured to move both axially, between the proximal and distal ends 202, 203, and also radially in a direction that is generally normal to the axial direction 207. In this manner, movement of the blocking element 209 in the distal direction 227 towards the distal end 203 of the housing 201 causes the blocking element 209 to simultaneously move radially inwards along a radially inward direction 223, whilst movement of the blocking element 209 in the proximal direction 226 towards proximal end 202 of the housing 201 causes the blocking element 209 to simultaneously move radially outwards along a radially outward direction 224. Movement of the blocking element 209 in the radially inward direction 223 causes the blocking element 209 to move closer towards the needle cover 118. Conversely, movement of the blocking element 209 in the radially outward direction 224 causes the blocking element 209 to move further away from the needle cover 118. Thus, the blocking element 209 can be moved along the inclined surface 204 of the housing 201 as desired to selectively move it closer to and further away from the needle cover 118 in the radial direction 223, 224.

When the blocking element 209 is arranged to be as close as possible to the proximal end 205 of the inclined surface 204 as is possible, such that it is at its maximum possible outwardly radial displacement along the radially outward direction 224, i.e. so that the blocking element 209 is as far apart from the needle cover 118 as is possible, the blocking element 209 and the needle cover 118 are in a clearance fit. When the blocking element 209 is arranged at the distal end 206 of the inclined surface 204 such that it is at its maximum possible inwardly radial displacement along the radially inward direction 223, i.e. so that the blocking element 209 is as close to the needle cover 118 as is possible, the blocking element 209 and the needle cover 118 are in an interference fit, and the blocking element 209 is thus configured to exert a clamping force 234 on the needle cover 118. This clamping force 234 can be used to selectively clamp the needle cover 118 in place, such that the friction between the blocking element 209 and the needle cover 118 provides a frictional force 233 which acts against the biasing force 130, to help retain the needle cover 118 in the retracted position and prevent it from inadvertently moving distally into the extended position, as described below.

The hold assistance device 200 may be configured such that the magnitude of the frictional force 233 is scaled as required, to be designed to be several times stronger than the biasing force 130 of the needle cover biasing member 120, to ensure that substantially all of the biasing force 130 is offset, to sufficiently aid the user in the operation of the medicament delivery system 300 by reducing the hold force required during injection. For example, the magnitude of the frictional force 233 may be scaled as required based on one or more of the angle θ 208, the coefficient of friction μ between the inclined surface 204 and the blocking element 209, and the coefficient of friction μ between the blocking element 209 and the needle cover 118. The angle θ 208 may for example be between approximately 3° and 45°. The coefficient of friction μ between the inclined surface 204 and the blocking element 209 may for example be between approximately 0.05 and 1, for example between approximately 0.05 and 0.5. The coefficient of friction μ between the blocking element 209 and the needle cover 118 may for example be between approximately 0.05 and 1, for example between approximately 0.05 and 0.5 In some examples, the biasing force 130 generated by the needle cover biasing member 120 may be between approximately 10 N and 15 N, and the magnitude of the frictional force 233 may be scaled accordingly to offset the biasing force 130.

Referring further to FIG. 4A, the hold assistance device 200 further comprises an actuation element 210 configured to cause the blocking element 209 to move along the inclined surface 204 as desired, to selectively provide the clamping force 234. The actuation element 210 is movable relative to the housing 201 and is also moveable relative to the blocking element 209. As shown in FIGS. 2 and 3, the actuation element 210 comprises a sleeve 211 which may be generally cylindrical and arranged to circumscribe the main body 102 of the injection device 100, such that the sleeve 211 is axially slidable around the main body 102. The sleeve 211 may be configured to be gripped by a user of the medicament delivery system 300, to allow the user to control the actuation element 210. Referring back to FIG. 4A, the actuation element 210 is circumscribed by the housing 201 such that at least a portion of the actuation element 210 is received inside the housing 201, whilst another portion of the actuation element 210 may protrude from the housing 201 for being gripped by a user of the hold assistance device 200.

The actuation element 210 may further comprise a flange 212 configured to sit against the inner surface 228 of the housing 201 to limit axial movement of the actuation element 210 in the proximal direction 226. That is, when the actuation element 210, which is axially slidable along the axial direction 207 relative to the housing 201, is at a maximum possible axial displacement in the proximal direction 226, it is prevented from moving any further in the proximal direction 226 towards the proximal end 128 of the medicament delivery device 100 by the flange 212 bearing against the inner surface 228 of the housing 201.

The actuation element 210 further comprises one or more arms 213 arranged to extend generally parallel to the axial direction 207, which are arranged inside the housing 201, such that when the hold assistance device 200 is coupled to a medicament delivery device 100, the arms 213 are arranged to extend in the distal direction 227 between the housing 201 and the main body 102. In the example shown, there are two arms 213. The subsequent description shall describe one of the arms 213, however it is to be understood that this description also applies to the other of the two arms 213 and indeed also to any additional arms 213 which may also be present. It is envisaged that there do not have to be two arms. There may be any number of one or more arms 213, for example one, two, three, four, five, six or more arms 213. In the example shown, the arms 213 are equally spaced apart from one another about the longitudinal axis 112 such that they are diametrically opposed to one another. Though, it is envisaged that the arms 213 may have any other suitable spatial arrangement. In the example shown, each of the arms 213 is integrally formed with or otherwise connected to the same sleeve 211, forming a single actuation element 210. Though, it is also envisaged that each of the arms 213 may be integrally formed with or otherwise connected to separate individual sleeves or actuation elements 210, such that more than one actuation element 210 may be present. In any case, the relationship of each of the actuation elements 210 and each of one or more blocking elements 209 is to actuate the blocking elements 209 and to be movable relative thereto and relative to the housing 201.

Turning back to the example of FIG. 4A, the actuation element 210 further comprises a head 214 integrally formed with or otherwise connected to the arm 213. The head 214 is arranged at a distal end of the arm 213 proximate to the distal end 203 of the housing 201. An exemplary form of the arm 213 and the head 214, and their movement relative to the blocking element 209, shall now be described with reference to three positions as shown in FIGS. 4A to 4C. These same positions are also shown in the enlarged views of FIGS. 5A to 5C, which show a zoomed in view of the arm 213 and the head 214.

The arm 213 of the actuation element 210 comprises an activation surface 215 and a release surface 216. In the example shown, the activation surface 215 and the release surface 216 are arranged to be generally normal to the axial direction 207 and are generally parallel to one another. The actuation element 210 also comprises a receiving space 217 for receiving the blocking element 209. The receiving space 217 comprises the activation surface 215 and the release surface 216. In the example shown, the arm 213 is generally elongate and the receiving space 217 is formed as a cut-out, recess or groove in the arm 213, with the activation surface 215 and the release surface 216 forming upper and lower or proximal and distal edges or surfaces of the receiving space 217. The head 214 comprises an angled edge 218, and the head 214 is formed from a flexible or resiliently deformable material, such that the angled edge 218 may be deflected around the blocking element 209 upon axial movement of the actuation element 210 in the distal direction 227, to deflect the arm 213 around the blocking element 209, causing the head 214 to hook under or clip under the blocking element 209. The blocking element 209 may comprise a cut-out 220 for receiving the head 214, such that the head 214 may hook into or clip into the blocking element 209.

FIGS. 4A and 5A show the actuation element 210 in a pre-activated position. When the hold assistance device 200 is coupled to a medicament delivery device 100, the actuation element 210 is configured to be in the pre-activated position when the needle cover 118 is in the extended position, for example before delivery of a medicament from the needle 116 has occurred. In the pre-activated position, the blocking element 209 is not arranged in its maximum possible radially inward position along the radially inward direction 223, such that the blocking element 209 and the needle cover 118 are in a clearance fit, and the needle cover 118 is free to axially slide relative to the main body 102, for example to move in the distal direction 227 under the action of the biasing force 130. When the actuation element 210 is in the pre-activated position, in the example shown, the angled edge 218 of the head 214 of the actuation element 210 is arranged to sit proximally above the blocking element 209, such that the blocking element 209 is arranged closer to the distal end 203 than the head 214, and the blocking element 209 is somewhat free to slide along the inclined surface 204, hence also the needle cover 118 may be free to axially move relative to the main body 102.

The direction of orientation of the inclined surface 204 however provides that it is easier for the needle cover 118 to move in the proximal direction 226 than in the distal direction 227. This is because the inclined surface 204 limits the movement of the blocking element 209, and the blocking element 209, when arranged at its maximum possible distal and radially inward displacement, provides friction against axial movement of the needle cover 118. The inclined surface 204 and the blocking element 209 can together function in a similar way to a sprag clutch or a door wedge, in that they more easily permit movement in one direction than in the opposite direction. That is, in the position shown in FIG. 4A, it is more difficult for the needle cover 118 to move in the distal direction 227 against the friction of the blocking element 209 than it is for the needle cover 118 to move in the proximal direction 226. This is because movement of the needle cover 118 in the distal direction 227 will pull the blocking element 209 further into or towards the distal end 206 of the inclined surface 204, and thus radially closer to the needle cover 118 along the radially inward direction 223. The blocking element 209 cannot slide any further along the inclined surface 204 once it is already at its maximum possible displacement towards the distal end 206 thereof, so the blocking element 209 is pulled further against the needle cover 118 with increasing force, thus providing further friction against the needle cover 118 and impeding its distal movement. Conversely, it is relatively less difficult for the needle cover 118 to move in the proximal direction 226 because movement of the needle cover 118 in the proximal direction 226 will push or drag the blocking element 209 away from the distal end 206 of the inclined surface 204 and towards the proximal end 205 thereof, and thus push it radially further apart from the needle cover 118 along the radially outward direction 224. Thus, the blocking element 209 can slide proximally up the inclined surface 204, so that it is pulled further away from the needle cover 118, thus providing reduced friction against the needle cover 118, and thus not resisting its proximal movement. In this manner, the orientation of the inclined surface 204 can provide a sprag-clutch like resistance of motion to the needle cover 118 by the action of the blocking element 209, such that inadvertent distal movement of the needle cover 118 will cause increased friction between the blocking element 209 and the needle cover 118, thus impeding said distal movement, whilst proximal movement of the needle cover 118 towards the proximal end 128 of the medicament delivery device 100 is not so much frictionally resisted.

Accordingly, the inclined surface 204 and the blocking element 209 together provide that movement of the needle cover 118 in the proximal direction 226 from the extended position towards the retracted position can be permitted, whilst movement of the needle cover 118 in the distal direction 227 from the retracted position towards the extended position can be impeded, thus counteracting the action of the biasing force 130 which serves to bias the needle cover 118 away from the retracted position towards the extended position. The inclined surface 204 and the blocking element 209, which together can function like a sprag-clutch as described above, can thus provide for the user hold force required to hold the needle cover 118 in the retracted position at an injection site for medicament delivery to take place, to be reduced, by offsetting the biasing force 130. However, it may be desirable to be able to selectively control when the blocking element 209 and the inclined surface 204 provide said function, such that the clamping force 234 can only be applied when necessary, thus reducing the frictional force 233 when required, so that when it is desired to permit the needle cover 118 to extend from the retracted position to the extended position, for example after medicament delivery has been complete, the blocking element 209 ceases or at least reduces its clamping function, such that the needle cover 118 is permitted to move into the extended position. To achieve this, the actuation element 210 serves to control the movement of the blocking element 209, and to selectively lock and unlock it into position as desired, as described below.

As outlined above, FIGS. 4A and 5A show the actuation element in a pre-activated position, in which the blocking element 209 is somewhat free to move along the inclined surface 204 in the proximal direction 226 and the distal direction 227, albeit still functions like a sprag clutch, to at least partially frictionally resist distal movement of the needle cover 118. In the pre-activated position, the head 214 is not hooked under or clipped under the blocking element 209. FIGS. 4B and 5B show the medicament delivery system 300 in a subsequent stage of operation, in which the needle cover 118 has been retracted inside the main body 102 into the retracted position, thus exposing the needle 116 (not shown), for example by pressing the medicament delivery device 100 against the skin of a patient at an injection site. The position shown in the examples of FIGS. 4B and 5B may therefore correspond with the time at which a medicament is being injected into a patient.

In the position shown in FIGS. 4B and 5B, the actuation element 210 is in an activated position in which the actuation element 210 applies an activation force to the blocking element 209 in the distal direction 227, i.e. towards the distal end 203 of the housing 201. When the actuation element 210 is in the activated position, the activation surface 215 is engaged with, for example to abut and press against, the blocking element 209, for example with an upper or proximal surface thereof. In the example shown, the receiving space 217 of the actuation element 210 is sized to be axially longer than the blocking element 209, such that the distance between the activation surface 215 and the release surface 216 along the axial direction 207 is greater than the length of the blocking element 209 along the axial direction 207. Thus, when the actuation element 210 is in the activated position, there is an activated position gap 221 (see FIG. 5B) between the blocking element 209 and the release surface 216.

When the actuation element 210 is in the activated position, the actuation element 210 is arranged closer to the distal end 203 of the housing 201 compared with when the actuation element 210 is in the pre-activated position. That is, in order to move the actuation element 210 from the pre-activated position to the activated position, the actuation element 210 is axially moved along the distal direction 227 towards the distal end 203 of the housing 201. Thus, distal axial movement of the actuation element 210, as the activation surface 215 bears against the blocking element 209, causes the blocking element 209 to also move along the distal direction 227. Due to the orientation of the inclined surface 204, this distal movement of the blocking element 209 also simultaneously causes the blocking 209 to move inwards along the radially inward direction 223, such that it is moved closer to the needle cover 118 and placed into increasing contact therewith to form an interference fit. Thus, movement of the actuation element 210 into the activated position causes the blocking element 210 to move against the inclined surface 204 towards the distal end 203 and to exert a clamping force 234 generally normal to the axial direction 207, along the radially inward direction 223, onto the needle cover 118. Accordingly, the blocking element 209 is locked in place by the actuation element 210, wedged between the inclined surface 204 of the housing 201 and the needle cover 118 by the activation surface 215, and the needle cover 118 is clamped in place in the retracted position such that it is prevented from inadvertently moving distally into the extended position, due to the frictional force 233 applied by the clamping action of the blocking element 209. By clamping the needle cover 118 in place and preventing it from inadvertently moving distally into the extended position by providing the frictional force 233, this counteracts the biasing force 130 of the needle cover biasing member 120 and thus reduces the magnitude of user hold force required to hold the medicament delivery device 100 at an injection site with the needle cover 118 in the retracted position.

The actuation element 210 may be kept in the activated position for as long as is needed for the user of the medicament delivery system 300 to deliver medicament from the needle 116 of the medicament delivery device 100 to an injection site of a patient, in order to reduce the amount of force needed to be applied by the user to retain the needle cover 118 in the retracted position in which the needle 116 is uncovered and can be used to deliver medicament. After delivery of the medicament from the needle 116 has been completed, the medicament delivery device 100 may be removed from the injection site of the patient, thus the hold force is no longer required. At this point, it may be desirable to recover the needle 116 with the needle cover 118 for safety and hygiene reasons, to help ensure safe removal and disposal of the medicament delivery device 100 from the injection site. Thus, it may be desired to bring the needle cover 118 back into the extended position in which it covers the needle 116. In order to allow the needle cover 118 to revert back into its extended position, under the action of the biasing force 130, the clamping force 234 can be removed, or at least reduced in magnitude, in order to reduce or remove the resistance provided by the frictional force 233 against the biasing force 130, such that the action of the needle cover biasing member 130 may be permitted to cause the needle cover 118 to move back into its extended position.

In order to reduce the magnitude of or remove the clamping force 234 in order to reduce the magnitude of the frictional force 233 in order to permit the needle cover 118 to revert back into its extended position, the actuation element 210 may be moved out of the activated position. Thus, next, once it is desired for the needle cover 118 to be permitted to move distally from the retracted position into the extended position, the clamping force 234 can be released, to reduce the frictional force 233 counteracting the biasing force 130. In order to do this, the blocking element 209 can be permitted to move in the proximal direction 226 towards the proximal end 205 of the inclined surface 204, so that it can move outwards, away from the needle cover 118, along the radially outward direction 224, to place the blocking element 209 and the needle cover 118 into a clearance fit rather than an interference fit.

FIGS. 4C and 5C show the actuation element 210 in a release position in which the actuation element 210 applies a release force to the blocking element 209 in the proximal direction 226. Movement of the actuation element 210 from the activated position into the release position permits the blocking element to move along the inclined surface 204 towards the proximal end 205 thereof. Thus, when the actuation element 210 is in the release position, movement of the actuation element 210 towards the proximal end 202 of the housing 201 causes the blocking element 209 to move along the inclined surface 204 away from the needle sleeve 118, thus reducing the magnitude of the clamping force 234. The frictional force 233 is thus reduced, such that the needle cover 118 may be permitted to move axially along the distal direction 227, biased into the extended position by the biasing force 130. Thus, movement of the actuation element 210 into the release position causes the counteracting frictional force 233 against the biasing force 130 to be substantially reduced or removed, such that the biasing force 130 is free to act on the needle cover 118, resulting in the needle cover 118 automatically extending back out into the extended position, thus safely and hygienically covering the needle 116.

The blocking element 209 is free to move along the inclined surface 204 in the proximal direction 226 and hence also in the radially outward direction 224 when the actuation element 210 is in the release position, because when the actuation element 210 is in the release position, the actuation element 210 no longer applies the activation force to the blocking element 209 in the distal direction 227 to force it downwards towards the distal end 206. Instead, when the actuation element 210 is in the release position, the actuation element 210 is pulled up relative to the blocking element 209, towards the proximal end 202 of the housing 201 in the proximal direction 226, such that the activation surface 215 no longer bears against the blocking element 209 and applies a force thereto. Instead, in the release position, the release surface 216 bears against the blocking element 209, for example against a lower or distal surface thereof, or for example by the head 214 being hooked into a cut-out 220 in the blocking element 209. In any case, as the actuation element 210 is caused to move in the proximal direction 226, for example by a user of the hold assistance device 200 pulling the sleeve 211 or another part of the actuation element 210 upwards towards the proximal end 128 by sliding the sleeve 211 relative to the main body 102, this pulls the activation surface 215 away from the blocking element 209 and pushes the release surface 216 towards the blocking element 209. As the actuation element 210 moves further along the proximal direction 226, since the release surface 216 is bearing against the blocking element 209, this causes the actuation element 210 to pull the blocking element 209 upwards in the proximal direction 226 towards the proximal end of the housing 202. As aforementioned, in the example shown, the receiving space 217 may be axially longer than the blocking element 209. Thus, when the actuation element 209 is in the release position, the activation surface 215 is spaced apart from the blocking element 209 by a release position gap 222 (see FIG. 5C).

The blocking element 209 can thus move axially within the receiving space 217 such that depending on the axial position of the actuation element 210, the activation surface 215 can apply an activation force, for example a pushing force, to cause the blocking element 209 to move towards the distal end 206 of the inclined surface 204. Conversely, the release surface 216 can apply a release force, for example a pulling force, to cause the blocking element 209 to move towards the proximal end 205 of the inclined surface 204. Accordingly, the actuation element 210 can pull the blocking element 209 up in the proximal direction 226 to pull it radially outwards away from the needle cover 118, in order to remove or at least reduce the clamping action on the needle cover 118.

The hold assistance device 200 can further comprise an actuation element biasing member 230, for example a spring 230, to bias the actuation element 210 towards the proximal end 202 of the housing 201. Thus, the actuation element 210 is biased in the proximal direction 226, and hence away from the activated position in which the actuation element 210 is arranged in a distal position. Thus, the actuation element 210 can be biased towards the pre-activated position and the release position. For example, the actuation element biasing member 230 may comprise a compression spring 230. When the actuation element 210 is arranged in a proximal position such that it is in the pre-activated position or the release position (see FIGS. 4A, 5A, 4C and 5C for example), the compression spring 230 is in a natural extended, uncompressed state. When the actuation element 210 is arranged in a distal position such that it is in the activated position (see FIGS. 4B and 5B for example), the compression spring 230 is compressed, due to the movement of the actuation element 210 in the distal direction 227 which compresses the spring 230. Hence, the compression spring 230 applies a biasing force 235 (see FIG. 4B) in the proximal direction 226, which serves to bias the actuation element 210 towards the proximal end 202 in the proximal direction 226. Thus, once the actuation element 210 has been placed into the activated position, the actuation element 210 is biased towards the release position. The hold force of a user operating the medicament delivery system 300 is configured to counteract the biasing force 235 to hold the actuation element 210 in the activated position, for example by pushing down on the actuation element 210 in the distal direction 227. For example, a user can slide or push the sleeve 211, or push down or otherwise apply a force onto some other part of the actuation element 210, to hold it in the activated position. When desired, for example after completion of delivery of a medicament, the user can remove or at least reduce said force, so that the biasing force 235 is no longer counteracted, thus causing the actuation element 210 to move in the proximal direction 226 from the activated position to the release position.

Figure 6:
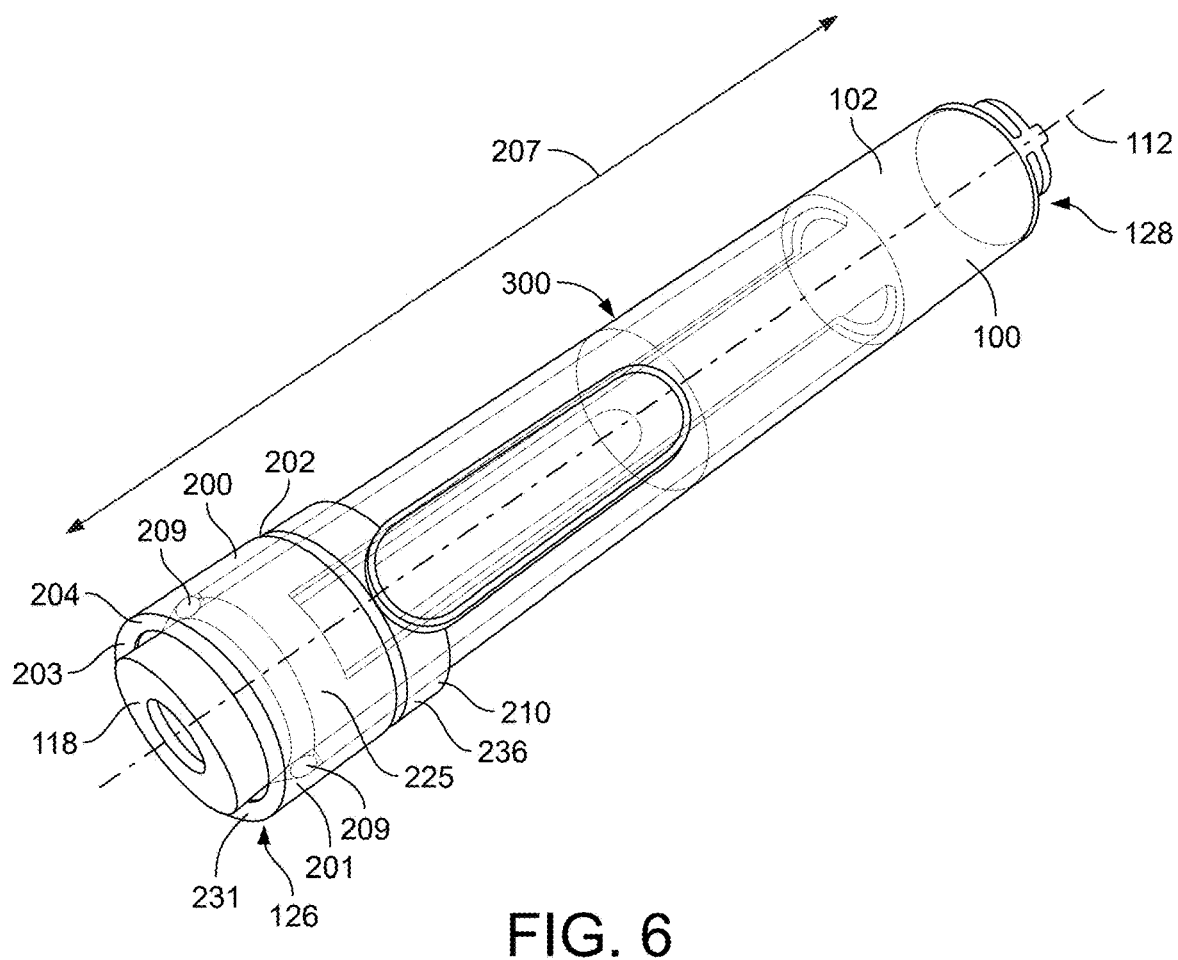
FIG. 6 shows a medicament delivery system.

FIG. 6 shows another example of a medicament delivery system, wherein like reference numerals denote like elements. In the example shown, the actuation element 210 comprises a push pad 236 arranged to circumscribe the main body 102 and the needle cover 118. The push pad 236 is relatively shorter in the axial direction 207 compared with the sleeve 211 in the example shown in FIGS. 4A to 5C and described above. The push pad 236 may be pushed down by a user to counteract the biasing force 235 to place the actuation element 210 into the activated position against the action of the actuation element biasing member 230. In order to move the actuation element 210 into the release position, the user may then release pressure on the push pad. It is envisaged that other forms of actuation element 210 are also possible.

Figures 7, 8:
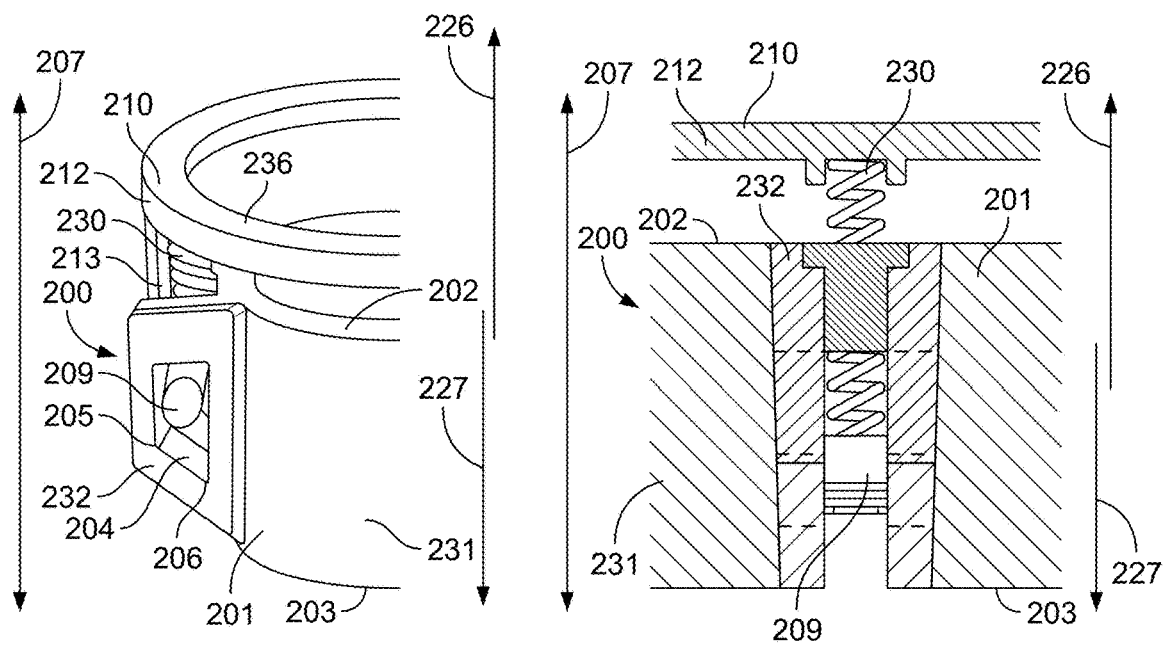
FIG. 7 shows a hold assistance device.
FIG. 8 shows a cross-sectional schematic view of a hold assistance device.
Figure 9A:
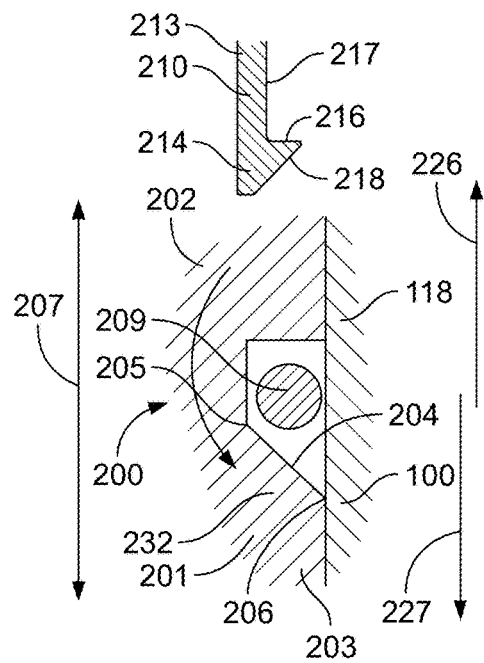
FIG. 9A shows a cross-sectional schematic view of a hold assistance device.
Figure 9B:
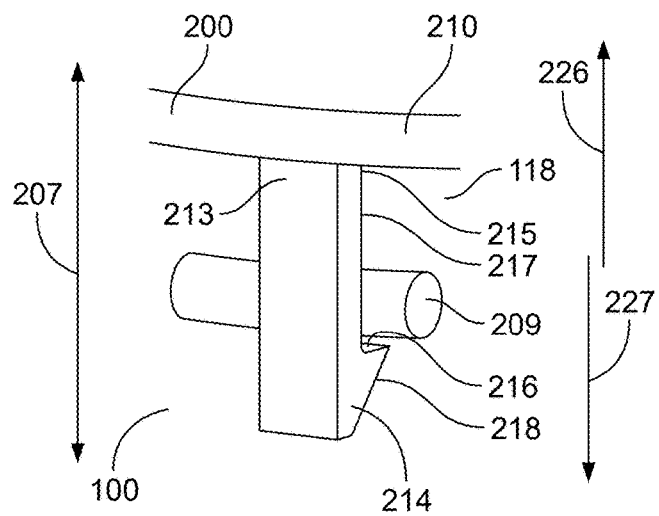
FIG. 9B shows a hold assistance device.

With further reference to the example of FIG. 6, as aforementioned, the blocking element 209 need not necessarily be in the form of one or more wedge shaped blocks and other shapes and arrangements are indeed also possible. For example, as shown in FIG. 6, there may be two blocking elements 209 each in the form of a cylinder configured to roll against the inclined surface 204, and wherein the head 214 of the actuation element 210 is configured to hook underneath the cylinder to pull the respective blocking element 209 in the proximal direction 226 from the activated position into the release position. FIGS. 7, 8 and 9A show the actuation element 210 in the pre-activated position. The push pad 236 can be pushed down in the distal direction 227 to move the actuation element 210 from the pre-activated position into the activated position, thus applying an activation force to the blocking element 219 in the distal direction 227 such that the blocking element 209 cylinder is caused to move distally and roll against the inclined surface 204 to exert a clamping force 234 in the radially inward direction 223. FIG. 9B shows the actuation element 210 in a distal position wherein the head 214 is hooked under the blocking element 209. The actuation element 210 can be pulled up in the proximal direction 226 to move the actuation element 210 from the activated position to the release position and hence move the blocking element 209 along the inclined surface 204 in a proximal 226 and radially outward 224 direction, to remove the clamping force 234 on and reduce the frictional force 233 on the needle cover 118.

Figure 10:
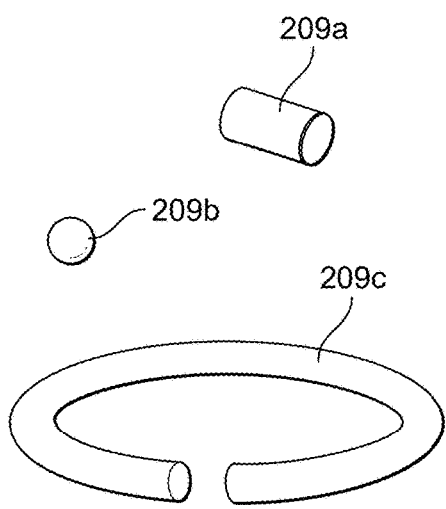
FIG. 10 shows three exemplary shapes of blocking element.

Other possible exemplary shapes of blocking element 209 are shown in FIG. 10. For example, the blocking element 209 may be in the form of a roller 209a, for example a cylinder, or the blocking element 209 may be in the form of a sphere 209b, for example a ball, or the blocking element 209 may be generally annular, for example in the form of a split ring 209c.

Figure 11:
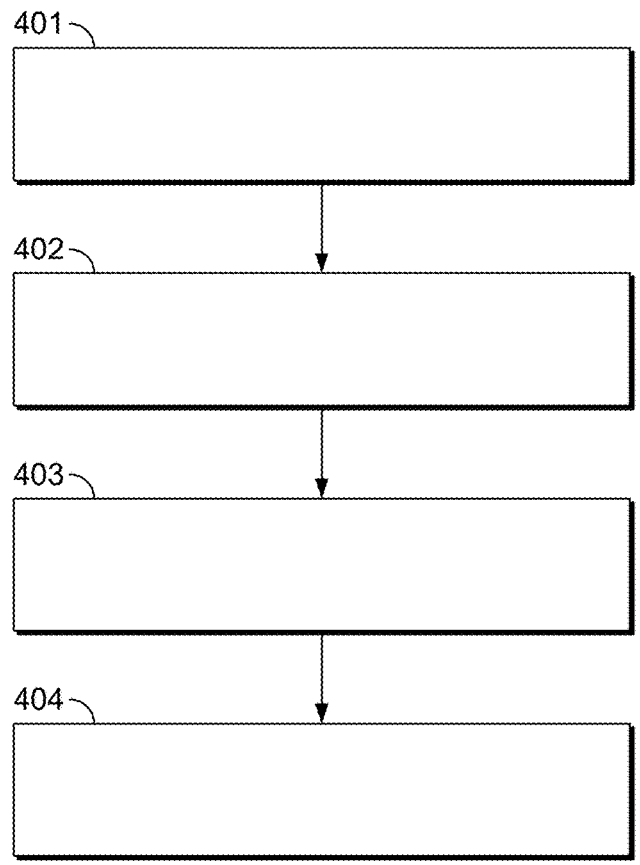
FIG. 11 shows a flowchart illustrating the steps of a method of operating a medicament delivery system.

FIG. 11 shows a flowchart depicting an exemplary method 400 of operating a medicament delivery system 300, for example medicament delivery systems 300 as described above. The exemplary method 400 of FIG. 11 comprises a step 401 of coupling the housing 201 to the main body 102, in order to couple the hold assistance device 200 to the medicament delivery device 100. In step 402, the needle cover 118 is moved from the extended position to the retracted position, such that, for example, the needle cover 118 is retracted inside the main body 102 such that the needle 116 is exposed, to place the medicament delivery device 100 in a state ready for medicament to be delivered from the needle 116 to an injection site of a patient.

In step 402, the needle cover 118 may be moved from the extended position to the retracted position for example by placing the medicament delivery device 100 against the skin of a patient at an injection site, and applying a force in the distal direction 227 in a direction towards the injection site, thus pushing the needle cover 118 against the skin and causing it to be pushed inside the main body 102 to retract thereinside.

Step 403 of the method 400 comprises moving the actuation element 210 into the activated position such that the blocking element 209 exerts the clamping force 234 on the needle cover 118. Step 403 may occur after step 402, or step 403 may occur simultaneously with step 402. In either case, it may be the occurrence of step 402 that may cause step 403 to happen. For example, moving the needle cover 118 from the extended position to the retracted position may cause the actuation element 210 to be automatically moved into the activated position. As another example, after or during moving the needle cover 118 from the extended position to the retracted position, a user of the medicament delivery system 300 may manually move the actuation element 210 into the activated position. For example, a user pushing the medicament delivery device 100 against an injection site of a patient to move the needle cover 118 from the extended position to the retracted position may cause the user to simultaneously apply a pushing force to the actuation element 210 to cause it to move into the activated position.

Step 404 of the method comprises releases the clamping force acting on the needle cover by moving the actuation element 210 from the activated position into a release position in which the actuation element 210 applies a release force to the blocking element 209 in a direction towards the proximal end, such that movement of the actuation element 210 from the activated position into the release position permits the blocking element 209 to move along the inclined surface 204 towards the proximal end 202. When the actuation element 210 is in the release position, movement of the actuation element 210 towards the proximal end 202 causes the blocking element 209 to move along the inclined surface 204 towards the proximal end 202, thus reducing the magnitude of the clamping force 234. For example, as outlined above, the actuation element 210 may comprise a release surface 216. When the actuation element 210 is in the release position, the release surface 216 may bear against the blocking element 209, for example against a lower or distal surface thereof, or may otherwise apply a force to the blocking element 209, for example by the head 214 being hooked into a cut-out 220 in the blocking element 209. As the actuation element 210 moves further along the proximal direction 226, since the release surface 216 is bearing against the blocking element 209, this causes the actuation element 210 to pull the blocking element 209 upwards in the proximal direction 226 towards the proximal end of the housing 202.

In the method 400, between step 403 of moving the actuation element 210 into the activated position and step 404 of releasing the clamping force 234 acting on the needle cover 118, a user of the medicament delivery system 300 may hold the medicament delivery device 100 for a required duration of time at an injection site of a patient. For example, the user may hold the medicament delivery device 100 at the injection site for the amount of time required for completion of delivery of a medicament from the needle 116 to be complete.

Once the actuation element 210 has been moved into the release position, the method 400 may further comprise a step (not shown) of moving the needle cover 118 from the retracted position back into the extended position, such that the needle 116 is covered, which may be desirable for reasons of safety and hygiene. The needle cover 118 may be moved from the retracted position back into the extended position by, for example, removing a user hold force acting on the medicament delivery device 100, for example by moving the medicament delivery device 100 away from an injection site of a patient. For example, by moving the medicament delivery device 100 in the proximal direction 226 away from the skin of a patient, this may remove the user hold force pushing the needle cover 118 inside the housing 102 as a result of pressing the needle cover 118 against the skin, such that when the medicament delivery device 100 is moved away, the needle cover 118 is permitted to extend outwards again under the action of the biasing force 130 of the needle cover biasing member 120, which is no longer offset by the frictional force 233 and the clamping force 234, since the actuation element 210 has been placed into the release position to move the blocking element 209 out from its clamping position.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term, "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

100—injection device
102—outer casing/housing/main body
104—reservoir
106—plunger
108—collar
110—cap
112—longitudinal axis
113—stopper
114—rear casing
116—needle
118—needle shroud/sleeve/cover
120—control spring/needle cover biasing member
122—drive spring
126—distal end
128—proximal end
130—biasing force
200—hold assistance device
201—housing
202—proximal end of housing
203—distal end of housing
204—inclined surface
205—proximal end of inclined surface
206—distal end of inclined surface
207—axial direction
208—angle θ
209—blocking element
209a—roller
209b—sphere
209c—split ring
210—actuation element
211—sleeve
212—flange
213—arm
214—head
215—activation surface
216—release surface
217—receiving space
218—angled edge of actuation element head
219—inclined surface of blocking element
220—cut-out
221—activated position gap
222—release position gap
223—radially inward direction
224—radially outward direction
225—receiving volume
226—proximal direction
227—distal direction
228—inner surface
229—outer surface
230—actuation element biasing member
231—cylindrical body
232—side portion
233—frictional force
234—clamping force
235—biasing force
236—push pad
300—medicament delivery system
400—method
401—method step
402—method step
403—method step
404—method step

The invention claimed is:

1. A hold assistance device for use with a medicament delivery device, the hold assistance device comprising:
a housing configured to be fixedly coupled to a medicament delivery device, the housing comprising proximal end and a distal end defining an axial direction, and an inclined surface angled relative to the axial direction;
a blocking element moveable along the inclined surface;
an actuation element moveable relative to the housing and arrangeable in an activated position in which the actuation element applies an activation force to the blocking element in a direction towards the distal end, such that movement of the actuation element into the activated position causes the blocking element to move against the inclined surface towards the distal end and to exert a clamping force generally normal to the axial direction; and
an actuation element biasing member configured to bias the actuation element towards the proximal end of the housing, wherein the actuation element biasing member comprises a spring.

2. The hold assistance device of claim 1, wherein when the actuation element is in the activated position, movement of the blocking element against the inclined surface towards the proximal end is resisted.

3. The hold assistance device of claim 1, wherein when the actuation element is in the activated position, the blocking element is wedged against the inclined surface by the actuation element.

4. The hold assistance device of claim 1, wherein when the housing is coupled to a medicament delivery device and the actuation element is in the activated position, the clamping force is configured to act on the medicament delivery device.

5. The hold assistance device of claim 1, wherein the hold assistance device comprises a receiving volume for receiving a medicament delivery device, and the clamping force is configured to act towards the receiving volume.

6. The hold assistance device of claim 1, wherein the activation force is configured to act in an axial direction towards the distal end.

7. The hold assistance device of claim 1, wherein movement of the actuation element into the activated position causes the blocking element to move in a radially inward direction that is generally normal to the axial direction.

8. The hold assistance device of claim 1, wherein the actuation element is axially movable relative to the housing.

9. The hold assistance device of claim 1, wherein the housing comprises an inner surface and an outer surface, the inner surface configured to be fixedly coupled to a medicament delivery device, wherein the inclined surface is arranged to be inclined inwards away from the outer surface and towards the inner surface in a direction away from the proximal end and towards the distal end.

10. The hold assistance device of claim 1, wherein the actuation element is arrangeable in a release position in which the actuation element applies a release force to the blocking element in a direction towards the proximal end, such that a movement of the actuation element from the activated position into the release position permits the blocking element to move along the inclined surface towards the proximal end, wherein when the actuation element is in the release position, movement of the actuation element towards the proximal end causes the blocking element to move relative to the inclined surface towards the proximal end, thus reducing a magnitude of the clamping force.

11. The hold assistance device of claim 10, wherein the actuation element comprises an activation surface for engaging with a proximal end of the blocking element to apply the activation force to the blocking element, and a release surface for engaging with a distal end of the blocking element to apply the release force to the blocking element.

12. The hold assistance device of claim 11, wherein the actuation element comprises a receiving space for receiving the blocking element, wherein the receiving space comprises the activation surface and the release surface.

13. The hold assistance device of claim 12, wherein the receiving space is axially longer than the blocking element, such that when the actuation element is in the activated position the activation surface is in contact with the blocking element but the release surface is not in contact with the blocking element, and such that when the actuation element is in the release position the release surface is in contact with the blocking element but the activation surface is not in contact with the blocking element.

14. The hold assistance device of claim 11, wherein the actuation element is arrangeable in a pre-activated position in which neither the activation surface nor the release surface is engaged with the blocking element, such that a movement of the actuation element from the pre-activated position into the activated position causes the activation surface to engage with the blocking element, and such that a movement of the actuation element from the activated position into the release position causes the release surface to engage with the blocking element.

15. The hold assistance device of claim 10, wherein movement of the actuation element from the activated position to the release position permits the blocking element to move in a radially outward direction that is generally normal to the axial direction.

16. The hold assistance device of claim 1, wherein the blocking element comprises a roller, a ball, a split ring, a block, and/or a wedge.

17. A medicament delivery system comprising a hold assistance device and a medicament delivery device,
wherein the hold assistance device comprises:
a housing configured to be fixedly coupled to a medicament delivery device, the housing comprising proximal end and a distal end defining an axial direction, and an inclined surface angled relative to the axial direction;
a blocking element moveable along the inclined surface; and
an actuation element moveable relative to the housing and arrangeable in an activated position in which the actuation element applies an activation force to the blocking element in a direction towards the distal end, such that movement of the actuation element into the activated position causes the blocking element to move against the inclined surface towards the distal end and to exert a clamping force generally normal to the axial direction,
wherein the medicament delivery device comprises:
a main body configured to receive a medicament cartridge and comprising a proximal end and a distal end;
a needle for delivery of medicament from the medicament cartridge;
a needle cover axially movable relative to the main body between:
an extended position in which the needle cover extends from the distal end of the main body and covers a distal end of the needle which protrudes from the main body, and a retracted position in which the needle cover is arranged in a proximal position relative to the extended position such that the distal end of the needle protrudes from a distal end of the needle cover; and
a needle cover biasing member configured to bias the needle cover axially in the distal direction towards the extended position,
wherein the housing of the hold assistance device is configured to be coupled to the main body, and when the housing is coupled to the main body, the clamping force is configured to act on the needle cover to resist movement of the needle cover axially in the distal direction towards the extended position.

18. The medicament delivery system of claim 17, wherein the medicament delivery system further comprises a medicament cartridge containing medicament.

19. A method of operating a medicament delivery system that comprises a hold assistance device and a medicament delivery device,
wherein the hold assistance device comprises:
a housing configured to be fixedly coupled to a medicament delivery device, the housing comprising proximal end and a distal end defining an axial direction, and an inclined surface angled relative to the axial direction;
a blocking element moveable along the inclined surface; and
an actuation element moveable relative to the housing and arrangeable in an activated position in which the actuation element applies an activation force to the blocking element in a direction towards the distal end, such that movement of the actuation element into the activated position causes the blocking element to move against the inclined surface towards the distal end and to exert a clamping force generally normal to the axial direction,
wherein the medicament delivery device comprises:
a main body configured to receive a medicament cartridge and comprising a proximal end and a distal end;
a needle for delivery of medicament from the medicament cartridge;
a needle cover axially movable relative to the main body between:
an extended position in which the needle cover extends from the distal end of the main body and covers a distal end of the needle which protrudes from the main body, and a retracted position in which the needle cover is arranged in a proximal position relative to the extended position such that the distal end of the needle protrudes from a distal end of the needle cover; and a needle cover biasing member configured to bias the needle cover axially in a distal direction towards the extended position, wherein the housing of the hold assistance device is configured to be coupled to the main body, and when the housing is coupled to the main body, the clamping force is configured to act on the needle cover to resist movement of the needle cover axially in the distal direction towards the extended position, wherein the method comprises:

coupling the housing to the main body;

moving the needle cover from the extended position to the retracted position;

moving the actuation element into the activated position such that the blocking element exerts the clamping force on the needle cover; and releasing the clamping force acting on the needle cover by moving the actuation element from the activated position into a release position in which the actuation element applies a release force to the blocking element in a direction towards the proximal end, such that movement of the actuation element from the activated position into the release position permits the blocking element to move along the inclined surface towards the proximal end, wherein when the actuation element is in the release position, a movement of the actuation element towards the proximal end causes the blocking element to move along the inclined surface towards the proximal end, thus reducing a magnitude of the clamping force.

* * * * *